United States Patent
Fang et al.

(10) Patent No.: US 10,648,031 B2
(45) Date of Patent: May 12, 2020

(54) PREPARATION OF ADAPTER-LIGATED AMPLICONS

(71) Applicant: QIAGEN GmbH, Hilden (DE)

(72) Inventors: Nan Fang, Neuss (DE); Dirk Loeffert, Haan (DE)

(73) Assignee: QIAGEN GmbH, Hilden (DE)

( * ) Notice: Subject to any disclaimer, the term of this patent is extended or adjusted under 35 U.S.C. 154(b) by 77 days.

(21) Appl. No.: 15/508,251

(22) PCT Filed: Aug. 21, 2015

(86) PCT No.: PCT/EP2015/069211
§ 371 (c)(1),
(2) Date: Mar. 2, 2017

(87) PCT Pub. No.: WO2016/034433
PCT Pub. Date: Mar. 10, 2016

(65) Prior Publication Data
US 2017/0283869 A1 Oct. 5, 2017

(30) Foreign Application Priority Data
Sep. 5, 2014 (EP) .................................. 14183695

(51) Int. Cl.
*C12Q 1/68* (2018.01)
*C12P 19/34* (2006.01)
*C12Q 1/6874* (2018.01)
*C12Q 1/6806* (2018.01)
*C12Q 1/6869* (2018.01)

(52) U.S. Cl.
CPC ............ *C12Q 1/6874* (2013.01); *C12P 19/34* (2013.01); *C12Q 1/6806* (2013.01); *C12Q 1/6869* (2013.01)

(58) Field of Classification Search
None
See application file for complete search history.

(56) References Cited

U.S. PATENT DOCUMENTS

| 5,604,097 A | 2/1997 | Brenner |
| 6,013,445 A * | 1/2000 | Albrecht .............. B01J 19/0046 435/6.11 |
| 2011/0319299 A1* | 12/2011 | Osborne ............ C12N 15/1093 506/26 |
| 2012/0172258 A1* | 7/2012 | Eshoo .................... C12N 15/10 506/26 |
| 2012/0283144 A1 | 11/2012 | Kucera et al. |

FOREIGN PATENT DOCUMENTS

| WO | 97/46704 A1 | 12/1997 |
| WO | 2009/072972 A1 | 6/2009 |
| WO | 2012/092265 A1 | 7/2012 |
| WO | 2013/082164 A1 | 6/2013 |

OTHER PUBLICATIONS

Illumina® "Preparing 2-5kb Samples for Mate Pair Library Sequencing," (42 pages) (Feb. 2009).
*New England BioLabs Inc.*® "FAQS," downloaded from https://www.neb.com/applications/cloning-and-synthetic-biology/~/media/6AEB0ECD517B4BEF843E23EDAA34FFF0.ashx on Jan. 17, 2019 (9 pages).
PNK Treatment of DNA Ends, OpenWetWare, https://openwetware.org/wiki/PNK_Treatment_of_DNA_Ends (2 pages) (Nov. 19, 2009).

\* cited by examiner

*Primary Examiner* — Tracy Vivlemore
*Assistant Examiner* — Sahana S Kaup
(74) *Attorney, Agent, or Firm* — Seed IP Law Group LLP

(57) ABSTRACT

The present invention is directed to novel methods and kits to be employed for preparing adapter-ligated amplicons or a sequencing library of a target DNA, respectively.

13 Claims, 5 Drawing Sheets
Specification includes a Sequence Listing.

SEQUENCE LISTING

<160> NUMBER OF SEQ ID NOS: 7

<210> SEQ ID NO 1
<211> LENGTH: 20
<212> TYPE: DNA
<213> ORGANISM: Artificial Sequence
<220> FEATURE:
<223> OTHER INFORMATION: PCR primer

<400> SEQUENCE: 1
cgggtaggcg ctctctatgt                                                    20

<210> SEQ ID NO 2
<211> LENGTH: 23
<212> TYPE: DNA
<213> ORGANISM: Artificial Sequence
<220> FEATURE:
<223> OTHER INFORMATION: PCR primer

<400> SEQUENCE: 2
aagactgaca atcccgtgta agg                                                23

<210> SEQ ID NO 3
<211> LENGTH: 58
<212> TYPE: DNA
<213> ORGANISM: Artificial Sequence
<220> FEATURE:
<223> OTHER INFORMATION: synthetic sequencing adapter

<400> SEQUENCE: 3
aatgatacgg cgaccaccga gatctacact ctttccctac acgacgctct tccgatct          58

<210> SEQ ID NO 4
<211> LENGTH: 63
<212> TYPE: DNA
<213> ORGANISM: Artificial Sequence
<220> FEATURE:
<223> OTHER INFORMATION: synthetic sequencing adapter
<220> FEATURE:
<221> NAME/KEY: modified_base
<222> LOCATION: 62
<223> OTHER INFORMATION: phosphorothioate

<400> SEQUENCE: 4
gatcggaaga gcacacgtct gaactccagt caccttgtaa tctcgtatgc cgtcttctgc        60
ttg                                                                      63

<210> SEQ ID NO 5
<211> LENGTH: 20
<212> TYPE: DNA
<213> ORGANISM: Artificial Sequence
<220> FEATURE:
<223> OTHER INFORMATION: PCR primer

<400> SEQUENCE: 5
aatgatacgg cgaccaccga                                                    20

<210> SEQ ID NO 6
<211> LENGTH: 21
<212> TYPE: DNA
<213> ORGANISM: Artificial Sequence
<220> FEATURE:
<223> OTHER INFORMATION: PCR primer

<400> SEQUENCE: 6
caagcagaag acggcatacg a                                                  21

```
<210> SEQ ID NO 7
<211> LENGTH: 22
<212> TYPE: DNA
<213> ORGANISM: Artificial Sequence
<220> FEATURE:
<223> OTHER INFORMATION: TaqMan probe
<220> FEATURE:
<221> NAME/KEY: modified_base
<222> LOCATION: 1
<223> OTHER INFORMATION: 6-carboxyfluorescein
<220> FEATURE:
<221> NAME/KEY: modified_base
<222> LOCATION: 22
<223> OTHER INFORMATION: tetramethylrhodamine

<400> SEQUENCE: 7
tgctgtggtg gacggccaat ga                                                22
```

PREPARATION OF ADAPTER-LIGATED AMPLICONS

STATEMENT REGARDING SEQUENCE LISTING

The Sequence Listing associated with this application is provided in text format in lieu of a paper copy, and is hereby incorporated by reference into the specification. The name of the text file containing the Sequence Listing is 770025.474USPC_SEQUENCE_LISTING.txt. The text file is 1.85 KB, was created on Feb. 27, 2017, and is being submitted electronically via EFS-Web.

The present invention is directed to novel methods and kits to be employed for preparing adapter-ligated amplicons or sequencing libraries of a target DNA, respectively.

FIELD OF THE INVENTION

The present invention relates to the field of molecular biology, more particularly to the preparation of adapter-ligated amplicons and, specifically, to the preparation of a sequencing library of a target DNA, respectively.

BACKGROUND OF THE INVENTION

Adapter-ligated amplified DNA fragments are required for many applications in modern molecular biology techniques. For example, adapter-ligated amplicons constitute libraries of a target DNA intended for sequencing analyses. The target regions in a DNA sample are subjected to an amplification procedure, e.g. by a polymerase chain reaction (PCR). The amplicons resulting from the PCR are subsequently ligated to adapter-molecules. The adapter-ligated amplicons or fragments of the target DNA are then subjected to a sequencing reaction. The DNA adapter molecules may therefore be provided with a nucleotide sequence that is specific for the sequencing primers. The resulting population of adapter-ligated amplicons is referred to as a so-called library, especially an amplicon sequencing library.

Currently, there are several common methods to generate amplicon sequencing libraries.

One method uses conventional multi-step enzymatic reactions to ligate adapters to the amplicons. This method is e.g. disclosed in Illumina Manual, "Mate Pair Library Preparation", 2009. Amplicons are generated with target-specific primers by PCR and then end-repaired. The end-repair step normally requires two enzymes: A polynucleotide kinase, normally the T4 polynucleotide kinase (PNK), that phosphorylates the 5'-terminus of the double stranded amplicon or PCR product, respectively, and enzymes with polymerase and exonuclease activities that make the ends of the PCR products blunt by either fill-in and trimming reactions. After the end-repair step, for sequencing on some platforms, such as those provided by Illumina®, an addition of adenine nucleotides is required by a so-called A-addition step. In this step an A-overhang is added to the 3'-terminus of the end-repaired PCR product, e.g. by Klenow fragment exo-, the large fragment of the DNA polymerase I having 5'→3' polymerase activity but lacking both 3'→5' exonuclease activity and 5'→3' exonuclease activity. This is to generate a docking side for the sequencing adapters that have an overhang formed by thymidine nucleotides, i.e. a T-overhang. After the A-addition, the sequencing adapter can be ligated to the amplicon by a DNA ligase, normally the T4 DNA ligase. For other sequencing platforms such as those from Life Technologies®, e.g. Ion Torrent PGM or Proton, SOLid, the A-addition step is not needed and blunt-ended adapters are ligated directly to the end-repaired amplicons.

Another library preparation method is to use fusion primers that contain both a target specific sequence and a part of the adapter sequences. After the first round of the PCR and the amplification of the target-specific regions, a second round of the PCR can be performed with primers containing the complete adapter sequence to add the adapter sequence to the amplicon.

Document WO 2009/072972 discloses a method for the enzymatic ligation of dsRNA adapter molecules to a dsRNA molecule.

All these methods in the art are tedious and time-consuming. Moreover, the method using fusion primers could also post challenge on design of the suitable PCR primers that should amplify hundreds to thousands of amplicons in the same multiplex PCR reactions without generating extensive amount of non-specific products.

Against this background, it is an object of the present invention to provide for a method of preparing adapter-ligated amplicons where the problems associated with the prior art methods can be reduced or avoided. It is also an object of the present invention to provide for an improved method of preparing a sequencing library of a target DNA.

The present invention satisfies these and other needs.

SUMMARY OF THE INVENTION

The present invention provides a method of preparing adapter-ligated amplicons, comprising the steps of:
(i) contacting double-stranded amplicons with
   at least one polynucleotide kinase,
   at least one DNA ligase, and
   DNA adapter molecules,
   to obtain a reaction mixture,
(ii) incubating said reaction mixture under conditions simultaneously allowing
   a 5' phosphorylation of said double-stranded amplicons by said polynucleotide kinase, and
   a joining of said DNA adapter molecules to at least one end of said double-stranded amplicons by said DNA ligase,
   to obtain adapter-ligated amplicons.

The present invention also provides a method of preparing a sequencing library of a target DNA, comprising the steps of:
(i) subjecting said target DNA to a PCR under conditions resulting in double-stranded PCR amplicons of said target DNA,
(ii) contacting said double-stranded PCR amplicons with
   at least one polynucleotide kinase,
   at least one DNA ligase, and
   DNA adapter molecules,
   to obtain a reaction mixture,
(iii) incubating said reaction mixture under conditions simultaneously allowing
   a 5' phosphorylation of said double-stranded PCR amplicons by said polynucleotide kinase, and
   a joining of said DNA adapter molecules to at least one end of said double-stranded PCR amplicons by said DNA ligase,
   to obtain a sequencing library of said target DNA.

The inventors have surprisingly realized that after amplifying a target DNA by an amplification method the resulting amplicons can be directly ligated with adapter molecules, such as sequencing platform-specific adapters, in one step, without intermediate modification steps, in particular eliminating the commonly required end-repair and A-addition steps which are time-consuming and inefficient.

Therefore, in step (i) of the method of preparing adapter-ligated amplicons and in step (ii) of the method of preparing a sequencing library of a target DNA the double-stranded amplicons are provided in a configuration directly resulting from the preceding amplification reaction without a subsequent chemical modification of the 3' and/or 5' termini, i.e. without the subsequent addition or removal of nucleotides (e.g. adenine or thymidine nucleotides), phosphate groups etc.

The methods according to the invention will allow the generation of adaptor-ligated amplicons or a sequencing library of a target DNA in only one step and will significantly reduce the working time. The obtained adapter-ligated DNA amplicons can then be used in conventional platforms, e.g. for next generation sequencing (NGS).

As used herein, a "double-stranded amplicon" refers to a piece of DNA that is the source or product of an amplification of DNA by a molecular amplification method, such as polymerase chain reaction (PCR), loop-mediated isothermal amplification (LAMP), strand displacement amplification (SDA), helicase-dependent amplification (HDA), nicking enzyme amplification reaction (NEAR). In this context, "amplification" refers to the production of one or more copies of a genetic fragment or target sequence, specifically the amplicon. The product of an amplification reaction, the amplicon, is used interchangeably with common laboratory terms, such as amplification product.

As used herein, "target DNA" refers to any double-stranded DNA (dsD-NA) of interest that may be subjected to an amplification method for generating double-stranded amplicons. "Target DNA" can be derived from any in vivo or in vitro source, including from one or multiple cells, tissues, organs, or organisms, whether living or dead, whether prokaryotic or eukaryotic, or from any biological or environmental source. Typically but not exclusively, "target DNA" refers to such dsDNA a nucleotide sequence is to be elucidated by sequencing, e.g. NGS.

As used herein, a "sequencing library" is a collection of target DNA fragments or target DNA amplicons, respectively. Usually said collection may be stored and propagated in a population of micro-organisms through the process of molecular cloning. The term "library" may also refer to a population or organisms, each of which carries a target DNA fragment inserted into a cloning vector, or alternatively to the collection of all of the cloned vector molecules. According to the invention said library is intended to be used in a subsequent sequencing reaction for elucidating the nucleotide sequence of the target DNA.

As used herein, a "kinase" is a type of enzyme that transfers phosphate groups from high energy donor molecules, such as ATP, two specific substrates, a process referred to as phosphorylation. A "polynucleotide kinase" refers to a kinase having polynucleotides as its substrate, such as DNA or RNA, but also being capable to phosphorylate oligonucleotides or mononucleotides. An example for a prominent polynucleotide kinase is a product of the T4 bacteriophage, the T4 polynucleotide kinase.

As used herein, a "ligase" stands for an enzyme that can catalyze the joining of two large molecules by forming a new chemical bond, usually with accompanying hydrolysis of a small chemical group dependent on one of the larger molecules or the enzymes catalyzing the linking together of two components, e.g. enzymes that catalyze joining of C—O, C—S, C—N, etc. A "DNA ligase" refers to an enzyme that facilitates the joining of DNA strands together by catalyzing the formation of a phosphodiester bond. Examples for adequate DNA ligases encompass *E. coli* DNA ligase, T4 DNA ligase, DNA ligase I, DNA ligase III, DNA ligase IV, etc.

As used herein, a "DNA adapter molecule" refers to a double-stranded (ds) DNA molecule capable of being joined to one or both extremities of fragments of DNA. Typically, a "DNA adapter molecule" has a length of between approximately 5 to 100 bp. The configuration of the DNA adapter molecule as provided in steps (i) or (ii) of the methods according to the invention depends on the configuration of the amplicons. The DNA adapter molecule may be blunt-ended if the amplicons are provided in a blunt-ended configuration. The DNA adapter molecules may comprise a nucleotide overhang added to the 3' and/or 5' ends of the respective strands if the amplicons resulting from the amplification reaction have a complementary overhang added to the 3' and/or 5' ends of the respective strands. Exemplary overhangs are a T-overhang comprised by the DNA adapter molecule consisting of one or more thymidine nucleotides, and a complementary A-overhang comprised by the amplicons consisting of one or more adenine nucleotides, respectively.

As used herein, "at least one" means that more than one element may be used. For example the invention may comprise two, three, four, five, six, seven, or more different elements, such as kinases, ligases, polymerases, etc.

Unless defined otherwise, all technical and scientific terms used herein generally have the same meaning as commonly understood by one of ordinary skill in the art to which this invention belongs.

The conditions wherein a 5' phosphorylation of the double-stranded amplicons by said DNA ligase, and a joining of said DNA adapter molecules to at least one end of said double stranded amplicons by said DNA ligase are well-known to the skilled person. Such conditions provide an environment allowing both the polynucleotide kinase to exert its enzymatic activity and simultaneously the DNA ligase to exert its enzymatic activity. In addition, such conditions ensure that the amplicons, the polynucleotide kinase, the DNA ligase and the DNA adapter molecules will be able to interact allowing the formation of the adapter-ligated amplicons. Preferably such conditions are realized by the presence of phosphate donors such as NTPs, in particular ATP, salts and ions, such as $Mg^{++}$, etc. Some ligases may also require NAD as a cofactor.

The preparing of adapter-ligated amplicons also includes the concept of the generation of a library of adapter-ligated amplicons where the amplicons result from an amplification of fragmented target DNA. The amplified and adapter-ligated target DNA may be used for subsequent analysis such as DNA sequencing. The adapter-ligated amplicons may, therefore, form a sequencing library of a target DNA.

The objects underlying the invention are herewith completely solved.

The features, characteristics, and embodiments of the invention as set forth in the description apply to the method of preparing adapter-ligated amplicons as well as to the method of preparing a sequencing library of a target DNA correspondingly.

According to an embodiment of the methods according to the invention said double-stranded amplicons are double-stranded PCR amplicons.

This measure has the advantage that a well-established amplification method is employed which belongs to the standard tools of most molecular biological laboratories. "PCR amplicons" refer to amplification products generated by the use of a polymerase chain reaction (PCR). The term "PCR amplicon" can be interchangeably used with "PCR product".

According to an embodiment of the methods according to the invention said double-stranded PCR amplicons are resulting from a PCR using a DNA polymerase comprising terminal adenylyl transferase activity.

This measure has the advantage that the inventors utilize the terminal adenylyl transferase activity of the DNA polymerase to generate an A-overhang on the double-stranded PCR amplicons, preferably at the 3' terminus of the respective strands. The DNA adapter molecules provided in the subsequent contacting step (i) or (ii) may then comprise a T-overhang, preferably at the 3' terminus of the respective strands. The double-stranded PCR amplicons comprising the A-overhang will then hybridize to the DNA adapter molecules comprising a T-overhang. The double-stranded PCR amplicons hybridized to the DNA adapter molecules will then be covalently bound to each other by the ligation reaction.

According to a preferred embodiment of the methods of the invention said DNA polymerase comprising terminal adenylyl transferase activity is selected from the group consisting of: Taq polymerase, Klenow fragment, TopTaq polymerase, Tfl-Polymerase, Tma-Polymerase, Tne-Polymerase and Tth-Polymerase.

This measure has the advantage that such DNA polymerases are provided which have been proven suitable for realizing the invention.

According to a preferred embodiment of the invention, the DNA adapter molecule comprises a T-overhang.

In this context "T-overhang" refers to at least one or more thymidine nucleotides added to the 3' and or 5' ends of the respective strands of the DNA adapter molecule. According to a preferred embodiment the T-overhang is located at the 3' end, i.e. one or more thymidine nucleotides were added to the 3' terminus of the DNA adapter molecule. Due to the T-overhang the DNA adapter molecule is capable to hybridize to DNA fragments, such as said double-stranded amplicons, having a corresponding overhang of the complementary adenine nucleotide, i.e. an A-overhang. Said A-overhang may be located at the 3' or 5' end of the respective strands of the DNA fragments or double-stranded amplicons. In another preferred embodiment the A-overhang is located at the 3' end of the respective strands of the DNA fragments or amplicons, respectively. In the presence of a DNA ligase the DNA fragments or amplicons, respectively, and the DNA adapter molecules become ligated together, resulting in adapter-ligated amplicons.

According to an embodiment of the methods according to the invention said polynucleotide kinase is selected from the group consisting of: T4 polynucleotide kinase, .T4 polynucleotide kinase (3' phosphatase minus).

This measure has the advantage that such polynucleotide kinases are used which could be demonstrated as being particularly suitable for the invention.

In another embodiment of the methods according to the invention said DNA ligase is selected from the group consisting of T4 DNA ligase, T3 DNA ligase, T7 DNA ligase, E. coli DNA ligase, Taq DNA ligase, and 9° N DNA ligase.

This measure has the advantage that such a DNA ligase is provided which has been proven to provide optimum results.

According to another preferred embodiment of the methods according to the invention said DNA adapter molecules are sequencing DNA adapter molecules, preferably DNA adapter molecules for next generation sequencing (NGS).

This measure has the advantage that the resulting adapter-ligated amplicons are provided in a configuration allowing a subsequent elucidation of the nucleotide sequence, preferably within the context of NGS, on a conventional sequencing platform.

In another preferred embodiment of the methods according to the invention in step (i) of the method of preparing adapter-ligated amplicons, or in step (ii) of the method of preparing a sequencing library of a target DNA, said contacting is realized by subjecting said double-stranded amplicons, said at least one polynucleotide kinase, said at least one DNA ligase, and said DNA adapter molecules to one single reaction container.

This measure has the advantage, that it embodies the principle of a "one-step" method. Even though the methods according to the invention can be subdivided in a contacting step and an incubating step, respectively, this subdivision only intends to illustrate the chronological sequence of the method events. However, the user of the method is only required to create the reaction mixture under the prescribed conditions. After an incubating time span the adapter-ligated amplicons or the sequencing library of the target DNA are automatically generated, i.e. virtually in one step. In particular, no preceding modification steps performed to the double-stranded amplicons, such as end-repair and A-addition steps, are necessary.

In another embodiment of the methods according to the invention after step (ii) in the method of preparing adapter-ligated amplicons, or after step (iii) of the method of preparing a sequencing library of a target DNA, the following step (iii) or (iv) is performed: isolating adapter-ligated amplicons.

This measure has the advantage that the adapter-ligated amplicons are provided in a condition allowing a direct subjection of the latter to the sequencing reaction. "Isolation" in this context means the purification of the adapter-ligated amplicons by removing reactants such as the involved enzymes, salts, reaction buffer, impurities, etc. and to provide the amplicons in a condition ensuring a long-time storage or a subsequent reaction.

Another subject-matter of the present invention relates to a kit for preparing adapter-ligated amplicons, comprising:
(i) at least one polynucleotide kinase,
(ii) at least one DNA ligase,
(iii) DNA adapter molecules, preferably comprising a T-overhang,
(vi) reaction buffer configured to simultaneously allowing the enzymatic functioning of said at least one polynucleotide kinase and said at least one DNA ligase, and
(v) a manual for performing the method for preparing adapter-ligated amplicons according to the invention.

Another subject matter of the present invention relates to a kit for preparing a sequencing library of a target DNA, comprising:
(i) at least one DNA polymerase, preferably comprising terminal adenylyltransferase activity,
(ii) at least one polynucleotide kinase,
(iii) at least one DNA ligase,
(iv) DNA adapter molecules, preferably comprising a T-overhang,
(v) PCR buffer,
(vi) reaction buffer configured to simultaneously allowing the enzymatic functioning of said at least one polynucleotide kinase and said at least one DNA ligase, and
(vi) a manual for performing the method of preparing a sequencing library of a target DNA according to the invention.

The compositions of the reaction buffer can be easily determined by the person skilled in the art, e.g. on the basis of conventional polynucleotide kinase buffers and DNA ligase buffers and, if applicable, an individually adjusting the components. In a series of experiments the individual activities of both enzymes in a specific reaction buffer can be determined allowing the identification of the optimum buffer composition where both enzymes work properly. Such reaction buffer may contain phosphate donors such as NTPs, in particular ATP, salts and ions, such as Mg$^{++}$, etc. Some ligases may also require NAD as a cofactor. An example for a suitable reaction buffer is the Rapid Ligation Buffer of Enzymatics®, Beverly, Mass., USA, comprising in its final concentration 66 mM Tris-HCl, 10 mM MgCl$_2$, 1 mM DTT, 1 mM ATP, 7.5% PEG 6000, pH 7.6 at 25° C.

The features, characteristics, advantages and embodiments of the methods according to the invention apply to the kits according to the invention correspondingly.

It goes without saying that the above-mentioned features and the features which are still to be explained below can be used not only in the respective specified combinations, but also in other combinations or on their own, without departing from the scope of the present invention.

Further features, characteristics and advantages follow from the description of preferred embodiments and the attached figures.

In the figures:

FIG. 1 shows a scheme of the one-step construction of adapter-ligated PCR amplicons or the amplicon sequencing library according to the invention.

FIG. 2 shows a diagram presenting the results of a first illustrating experiment. In all four samples the IL1R2 amplicon is present in similar amounts (A). The reaction with both T4 DNA ligase and T4 PNK enables a direct ligation of sequencing adapters to the amplicon (B).

EXAMPLES

1. Principle of the Invention

Figure 1:
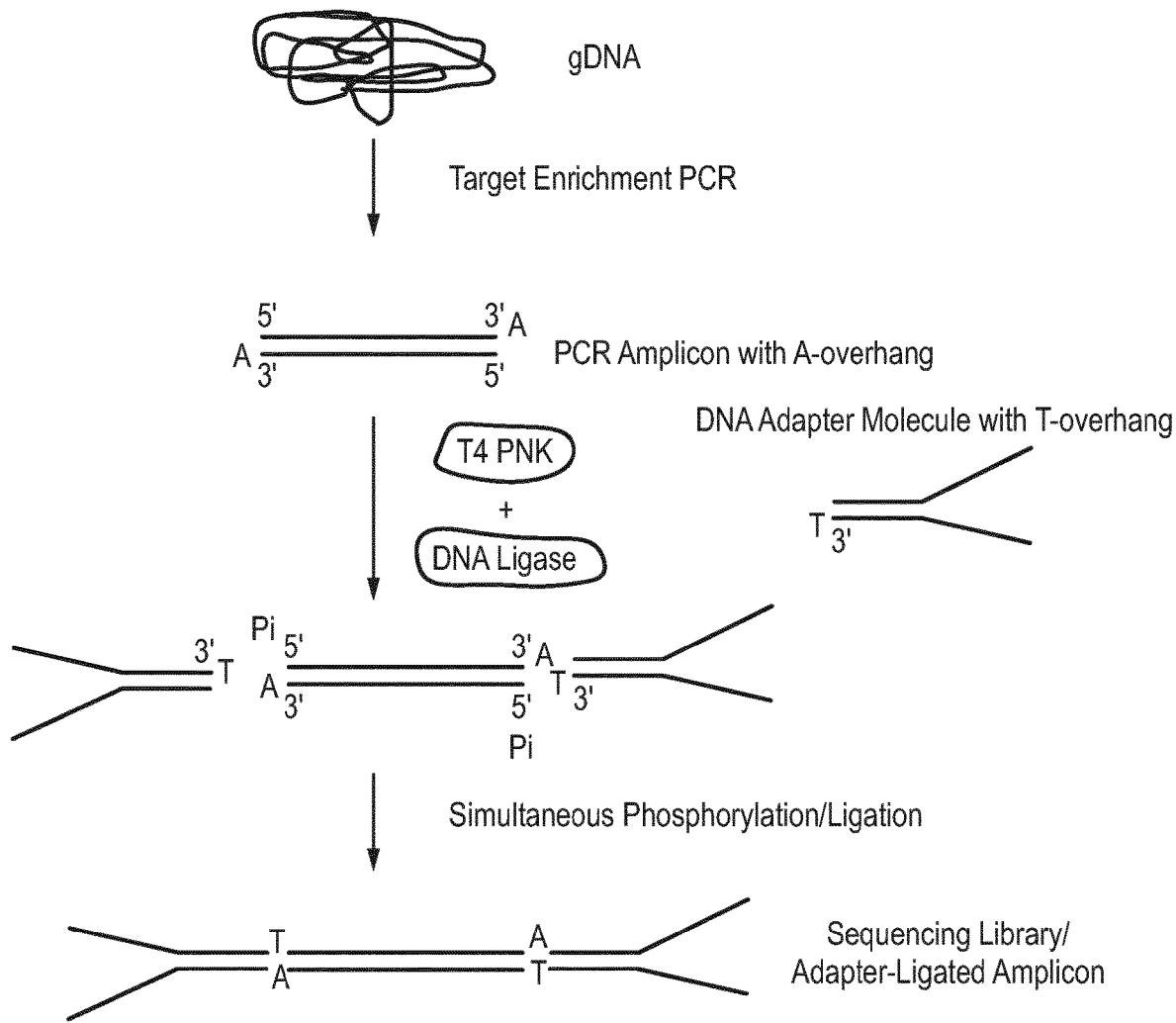

The aim of this invention is to circumvent tedious and time-consuming end-repair and A-addition steps in the next generation library preparation workflow for amplicon sequencing. The inventors utilize the terminal adenylyl transferase activity of the PCR polymerase to generate an A-overhang at the 3' termini of the amplicons during the PCR. Following PCR, the amplicons are subjected to a combined phosphorylation and ligation reaction. In this reaction, the amplicons with A-overhang are mixed with sequencing adapters containing a T-overhang at the 3' termini of the respective strands, polynucleotide kinase (PNK), such as the T4 PNK, DNA ligase, and incubated in reaction buffer that functions for both the ligase and kinase; cf. FIG. 1. In this scheme gDNA stands for genomic DNA and Pi stands for an inorganic phosphate residue.

2. Experimental Test 1

To prove the principle of the invention, the inventors used the method described above to perform a PCR employing Taq polymerase, and then directly ligated the amplicons to Illumina® TruSeq sequencing adapters, which have a T-overhang. Briefly, four identical 50 µl PCR reactions were set up with 10 ng of human genomic DNA each as a template, QIAGEN® HotStar Plus Master Mix (containing chemically modified Taq polymerase) at 1× final concentration, and 0.2 µM each of PCR primers that specifically recognize the human IL1R2 gene, IL1R2 F (Seq_1) and IL1R2 R (Seq_2). PCR cycling conditions were as follows: 95° C., 5 min for initial denaturation; then 35 cycles of 94° C., 30 sec; 60° C., 30 sec; and 72° C., 60 sec; followed by 72° C., 20 min for final extension and A-addition. Once the PCR was completed, the PCR reaction was cleaned up with QIAGEN® MinElute PCR Purification Kit and the PCR product from each reaction was eluted in 20 µl RNase-free water and pooled together. One duplicate of 19 µl of purified PCR products (sample 1 and sample 2) was then subjected to a combined phosphorylation and ligation reaction with 1× Rapid Ligation Buffer (Enzymatics®), 1 µM of Illumina® sequencing adapter that was generated by annealing two oligos to form a duplex (IDT, Seq_3 and Seq_4), 3 µl of T4 DNA ligase (T4 DNA Ligase Rapid, 600 U/µl, Enzymatics®) and 2 µl of T4 polynucleotide kinase (T4 PNK, 10 U/µl, New England Biolabs®). Another duplicate of 19 µl of purified PCR products (sample 3 and sample 4) were subjected to a ligation reaction only with above-mentioned components, however without the T4 poly-nukleotide kinase; cf. Table 1. All four reactions had a reaction volume of 50 µl and were carried out for 30 min at room temperature.

TABLE 1

Ct values of the ligation products (Sample 1 to Sample 4) that can be detected with qPCR primers recognizing either adapter sequences or IL1R2 amplicon sequences.

|  | Ligase | T4 PNK | Ct with Library Primers | Ct with IL1R2 Primers |
|---|---|---|---|---|
| Sample 1 | Yes | Yes | 13.96 | 8.07 |
| Sample 1 | Yes | Yes | 13.18 | 7.96 |
| Sample 2 | Yes | Yes | 13.83 | 7.7 |
| Sample 2 | Yes | Yes | 14.05 | 7.75 |
| Sample 3 | Yes | No | not detected | 8.16 |
| Sample 3 | Yes | No | not detected | 8.05 |
| Sample 4 | Yes | No | not detected | 7.79 |
| Sample 4 | Yes | No | not detected | 8.02 |

After the ligation reaction, the products were purified with QIAGEN® MinElute PCR purification kit and eluted in 20 µl of RNase-free water. The eluates were diluted with 1:1000 with RNase-free water and used as template in quantitative real-time PCR to detect the presence or absence of the ligation products. Two sets of primers were used: One set of the primers, library primer F and library primer R, recognizes Illumina® adapter sequences (Seq_5 and Seq_6); the other set of the primers is the same as used to generate the IL1R2 amplicon and recognizes all of the IL1R2 amplicon sequence (Seq_1 and Seq_2). A TaqMan probe with 5' FAM label (Seq_7) that specifically recognizes internal IL1R2 amplicon sequence was used in combination with either library primers or IL1R2 primers to quantify the amount of Illumina® adapter-ligated amplicon or total IL1R2 amplicon, respectively. The qPCR reactions were set up with QuantiFast Probe PCR mix (1× final concentration), 0.4 µM of each of the primers, 0.2 µM of the TaqMan probe, and 2 µl of diluted ligation products from sample 1 to sample 4. The qPCR was performed on QIAGEN® Rotorgene real time PCR cycler with the following cycling conditions: 95° C., 3 min; and 40 cycles of 95° C., 3 sec; 60° C., 30 sec.

Figure 2A:
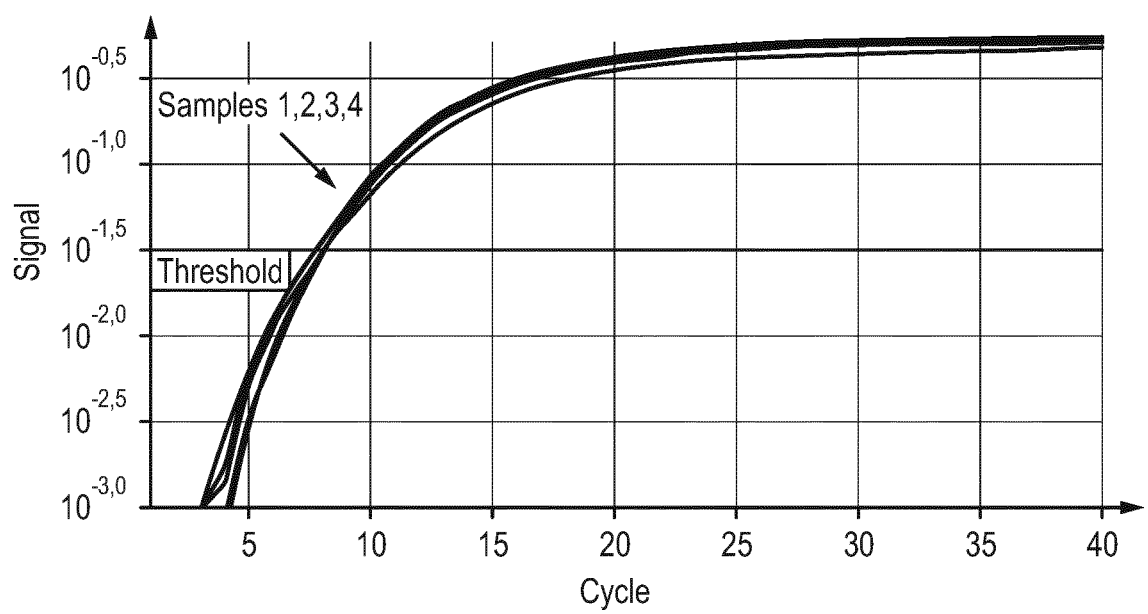
Figure 2B:
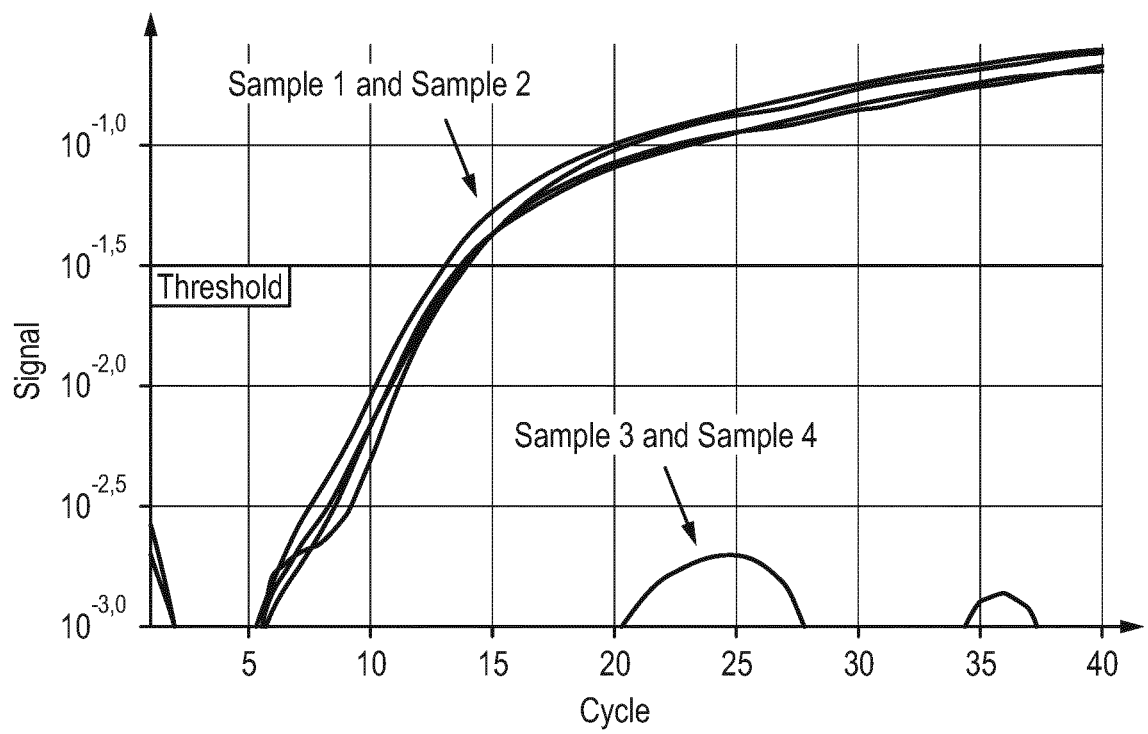

The result of this experiment is shown in FIG. 2 and Table 1. All four samples (in duplicates) showed similar Ct values in the qPCR with IL1R2 primers, indicating similar amounts of the total IL1R2 amplicons; FIG. 2A. However, only sample 1 and sample 2, where T4 PNK was present in the ligation reaction, showed positive signals with low Ct values in the qPCR reactions with library primers F and R, while sample 3 and sample 4, where ligation reaction was absent of T4 PNK, did not generate detectable qPCR products with library primers F and R; FIG. 2B.

The results positively proved the principle that next generation library for amplicon sequencing can be successfully and rapidly prepared with a one-step, combined phosphorylation and ligation step directly after the PCR, eliminating time-consuming and error-prone multiple enzyme steps that are commonly used in the art.

3. Experimental Test 2

The inventors further proved the principle of this invention with an amplicon sequencing experiment using the QIAGEN® GeneRead™ DNAseq Targeted Panel. The QIAGEN® GeneRead™ DNAseq Targeted Panel uses multiplex PCR to selectively amplify exons of the genes of interest. Following multiplex PCR, the amplicons need to be ligated with the platform-specific sequencing adapters for sequencing.

Figure 3A:
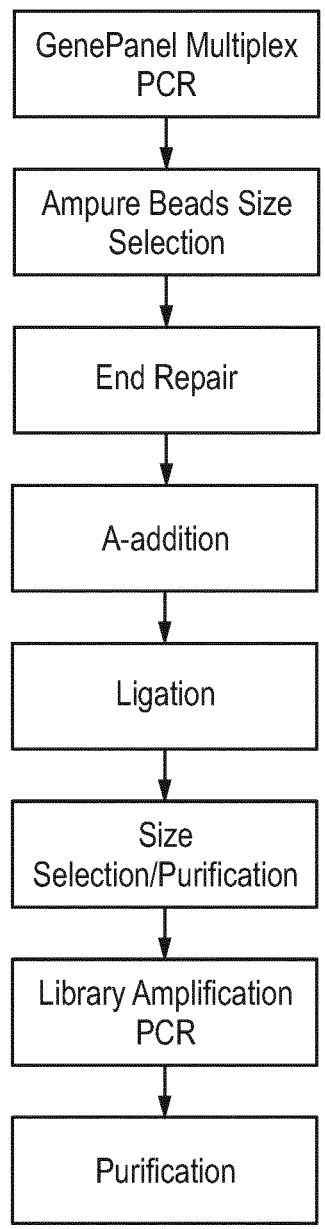
FIG. 3 shows a scheme illustrating the standard library prep construction work for Gene Read™ DNAseq targeted panels amplicon sequencing (A), and the one-step library prep construction workflow for Gene Read™ DNAseq targeted panels amplicon sequencing according to the invention (B).

The standard library construction method for target amplicon sequencing on Illumina® platforms involves three enzymatic steps: End-repair, A-addition, and ligation, in combination with several clean-up and size selection steps to remove non-specific side products. A PCR step after ligation is also included to amplify the sequencing library; cf. FIG. 3A, see also QIAGEN® GeneRead™ DNAseq Targeted Panels V2 handbook.

Figure 3B:
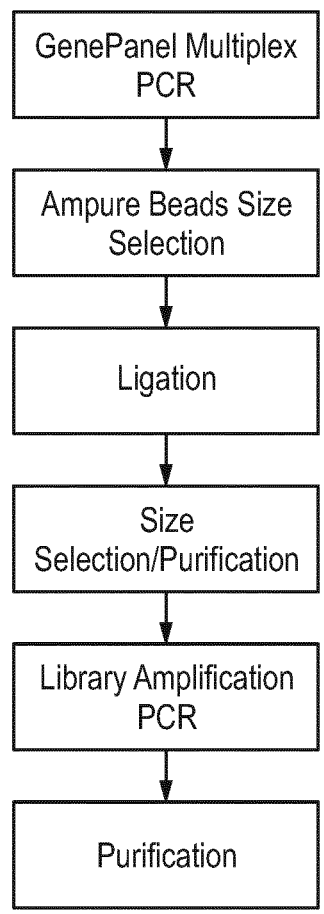

The inventors compared the performance of the one step library construction method according to the invention with the standard library construction protocol. The one-step method according to the invention is outlined in FIG. 3B. Specifically, human genomic DNA (gDNA) from an anonymous donor was used as template and amplified with QIAGEN® GeneRead™ Human Carrier Panel V2 (Cat. # NGHS-011X). Following multiplex PCR, the amplicons were either subjected to standard library prep workflow ('Control'), or one-step library prep protocol according to the invention ('OneStep'). With the one step protocol, the purified PCR products were directly ligated to adapters with 3 µl of T4 DNA ligase (T4 DNA Ligase Rapid, 600 U/µl, Enzymatics®) and 2 µl of T4 polynucleotide kinase (T4 PNK, 10 U/µl, New England Biolabs®) in 1× Rapid Ligation Buffer (Enzymatics®) with a final volume of 90 µl. The one-step reaction with combined phosphorylation and ligation was carried out for 30 min at room temperature. Both sequencing libraries were characterized with an Agilent® High Sensitivity DNA chip on the Bioanalyzer.

Figure 4A:
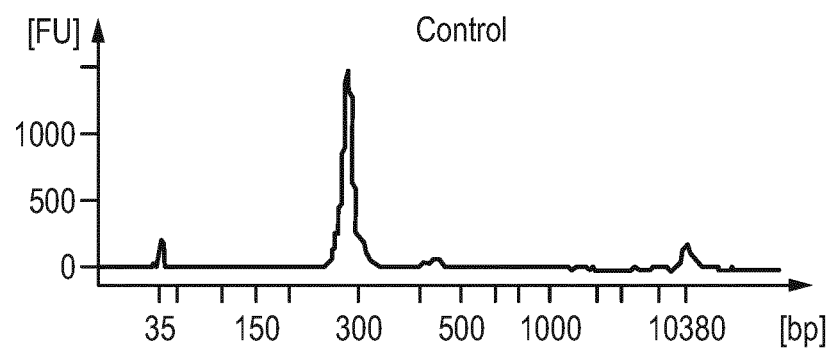
FIG. 4 shows the result of a second illustrating experiment. It was demonstrated that sequencing libraries generated with either the standard or the one-step method according to the invention show similar size distribution patterns.
Figure 4B:
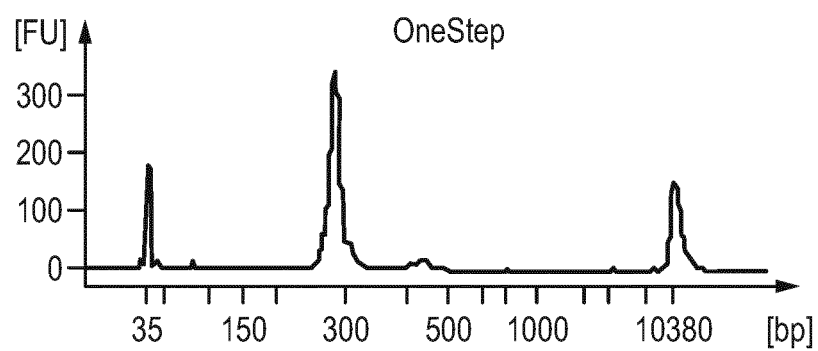

As shown in FIG. 4, the library constructed with the standard method ('Control') and the one-step method according to the invention ('OneStep') have very similar size distribution patterns.

The two libraries were then sequenced on a miSeq instrument (Illumina®) using dual-layer 300 nt Flow Cells and Illumina® miSeq Reage nt Kit V2 (300). Paired-end sequencing mode with 2×150 nt read length was used for the run. Data were analyzed with QIAGEN® GeneRead Targeted Exon Enrichment Panel Data Analysis tool.

The metrics for amplicon sequencing quality were summarized in Table 2 and demonstrated a good sequencing quality for amplicon sequencing libraries generated with both the standard method ('Control') and the novel one-step method according to the invention ('OneStep'). As shown in the Table 2, libraries generated by both standard and the novel method according to the invention delivered similarly good sequencing results based on the metrics, such as total reads, percentage of reads aligned to the target region and control amplicons, percentage of based covered at >=20% of median, percentage of bases covered at >=10×, 30×, or 100× coverage, as well as mean and median coverage.

TABLE 2

Sequencing quality metrics for amplicon sequencing libraries generated with either standard method ('Control') or one-step method ('OneStep').

| Sequencing Quality Metrics | Control | OneStep |
|---|---|---|
| Total reads | 3.088.012 | 4.030.836 |
| % Reads >= 45 bp aligned to the target region and control amplicons | 95.8 | 92.7 |
| % of bases covered at >= 20% of median | 83 | 81 |
| % of bases covered at >= 10× | 96 | 94 |
| % of bases covered at >= 30× | 91 | 88 |
| % of bases covered at >= 100× | 80 | 76 |
| total sequenced bases on target | 336.319.887 | 420.999.290 |
| mean coverage | 507 | 634 |
| median coverage | 364 | 355 |

4. Conclusion

Taken together, the novel one-step amplicon sequencing library prep method according to the invention has been demonstrated to be effective in generating a sequencing library with good quality. Furthermore, the one-step method also significantly streamlines the library prep workflow and can potentially reduce variations by remove multiplex enzymatics and handling steps in the protocol.

```
Sequences
                                           (SEQ ID NO: 1)
Seq_1: 5'-cgg gta ggc gct ctc tat gt-3'

(SEQ ID NO: 2)
Seq_2: 5'-aag act gac aat ccc gtg taa gg-3'

(SEQ ID NO: 3)
Seq_3: 5'-AATGATACGGCGACCACCGAGATCTACACTCTTTCCCTACA-
       CGACGCTCTTCCGATC*T-3'
       (*: indicates phosphorothioate)

(SEQ ID NO: 4)
Seq_4: 5'-
       GATCGGAAGAGCACACGTCTGAACTCCAGTCACCTTGTAATC-
       TCGTATGCCGTCTTCTGCTT*G-3'
       (*: indicates phosphorothioate)

(SEQ ID NO: 5)
Seq_5: 5'-AAT GAT ACG GCG ACC ACC GA-3'

(SEQ ID NO: 6)
Seq_6: 5'-CAA GCA GAA GAC GGC ATA CGA-3'

(SEQ ID NO: 7)
Seq_7: 5'-FAM-tgctgtggtggacggccaatga-TAMRA-3'
       (FAM stands for 6-carboxyfluorescein; TAMRA
       stands fortetramethylrhodamine)
```

The invention claimed is:

1. A method of preparing adapter-ligated amplicons, comprising the steps of:
   (i) contacting double-stranded amplicons with
      at least one polynucleotide kinase,
      at least one DNA ligase, and
      DNA adapter molecules,
   to obtain a reaction mixture, wherein the double-stranded amplicons are provided directly resulting from an amplification reaction without a subsequent chemical modification of the 3' and/or 5' termini, and
   (ii) incubating said reaction mixture under conditions simultaneously allowing
      a 5' phosphorylation of said double-stranded amplicons by said polynucleotide kinase, and
      a joining of said DNA adapter molecules to at least one end of said double-stranded amplicons by said DNA ligase,
   to obtain adapter-ligated amplicons.

2. The method of claim 1, wherein said double-stranded amplicons are double-stranded PCR amplicons.

3. The method of claim 2, wherein said double-stranded PCR amplicons result from a PCR using a DNA polymerase comprising terminal adenylyltransferase activity.

4. The method of claim 3, wherein said DNA polymerase is selected from the group consisting of: Taq polymerase, Klenow fragment, TopTaq polymerase, Tfl-Polymerase, Tma-Polymerase, Tne-Polymerase, and Tth-Polymerase.

5. The method of claim 1, wherein said DNA adapter molecules comprise a T overhang.

6. The method of claim 1, wherein said polynucleotide kinase is T4 polynucleotide kinase or T4 polynucleotide kinase (3' phosphatase minus).

7. The method of claim 1, wherein said DNA ligase is selected from the group consisting of: T4 DNA ligase, T3 DNA ligase, T7 DNA ligase, *E. coli* DNA Ligase, Taq DNA ligase, and 9° N DNA ligase.

8. The method of claim 1, wherein said DNA adapter molecules are sequencing DNA adapter molecules.

9. The method of claim 1, wherein in step (i), said contacting is realized by subjecting said double-stranded amplicons, said at least one polynucleotide kinase, said at least one DNA ligase, and said DNA adapter molecules to one single reaction container.

10. The method of claim 1, further comprising, after step (ii),
   (iii) isolating adapter-ligated PCR amplicons.

11. A method of preparing a sequencing library of a target DNA, comprising the steps of:
   (i) subjecting said target DNA to a PCR under conditions resulting in double-stranded PCR amplicons of said target DNA,
   (ii) contacting said double-stranded PCR amplicons with
      at least one polynucleotide kinase,
      at least one DNA ligase, and
      DNA adapter molecules,
   to obtain a reaction mixture, wherein the double-stranded amplicons are provided directly resulting from an amplification reaction without a subsequent chemical modification of the 3' and/or 5' termini, and
   (iii) incubating said reaction mixture under conditions simultaneously allowing
      a 5' phosphorylation of said double-stranded PCR amplicons by said DNA ligase, and
      a joining of said DNA adapter molecules to at least one end of said double-stranded PCR amplicons by said DNA ligase,
   to obtain a sequencing library of said target DNA.

12. The method of claim 1, wherein said DNA adapter molecules are DNA adapter molecules for next generation sequencing (NGS).

13. The method of claim 11, wherein said DNA adapter molecules comprise a T-overhang.

* * * * *